United States Patent
O'Meara et al.

(10) Patent No.: US 6,706,706 B2
(45) Date of Patent: Mar. 16, 2004

(54) NON-NUCLEOSIDE REVERSE TRANSCRIPTASE INHIBITORS

(75) Inventors: Jeffrey O'Meara, Laval (CA); Bruno Simoneau, Laval (CA); Christiane Yoakim, Laval (CA); Robert Déziel, Mont-Royal (CA); William W. Ogilvie, Ottawa (CA)

(73) Assignee: Boehringer Ingelheim International GmbH, Ingelheim (DE)

( * ) Notice: Subject to any disclaimer, the term of this patent is extended or adjusted under 35 U.S.C. 154(b) by 12 days.

(21) Appl. No.: 10/379,448

(22) Filed: Mar. 4, 2003

(65) Prior Publication Data

US 2003/0195197 A1 Oct. 16, 2003

Related U.S. Application Data

(60) Provisional application No. 60/367,971, filed on Mar. 27, 2002.

(51) Int. Cl.[7] ........................ C07D 47/14; A61K 31/55; A61P 31/18
(52) U.S. Cl. ........................ 514/220; 540/495
(58) Field of Search ................ 540/495; 514/220

(56) References Cited

U.S. PATENT DOCUMENTS

| | | |
|---|---|---|
| 5,705,499 A | 1/1998 | Cywin et al. |
| 6,420,359 B1 | 7/2002 | Simoneau .............. 514/220 |

FOREIGN PATENT DOCUMENTS

| | | |
|---|---|---|
| EP | 0 767 172 A1 | 4/1997 |
| WO | WO 01/96338 A1 | 12/2001 |
| WO | WO 02/076982 A2 | 10/2002 |
| WO | WO 03/011862 A1 | 2/2003 |

OTHER PUBLICATIONS

Benn, S. et al; "Genomic heterogeneity of AIDS Retroviral isolates from North America and Zaire"; Science; 1985, vol. 230, pp. 949–951.
Cywin, C. L. et al; "Novel Nonnucleoside Inhibitors of HIV–1 Reverse Transcriptase. 8. 8–Aryloxymethyl–and 8–Arylthiomethyldipyridodiazepinones1"; J Med Chem, 1998, vol. 41, pp. 2972–2984.
D'Aquila, R. T. et al; "HIV–1 Reverse Transcriptase/Ribonuclease H: High Level Expression in *Escherichia coli* from a Plasmid Constructed Using the Polymerase Chain Reaction"; J Acquired Immune Deficiency Syndrome; 1989, vol. 2; pp. 579–587.
Hargrave, K. D. et al; "Novel Non–Nucleoside Inhibitors of HIV–1 Reverse Transcriptase. 1. Tricyclic Pyridobenzo–and Dipyridodiazepinones"; J Med Chem, 1991, vol. 34, pp. 2231–2241.
Klunder, J. M. et al; "Novel Nonnucleoside Inhibitors of HIV–1 Reverse Transcriptase. 7. 8–Arylethyldipyridodiazepinones as Potent Broad–Spectrum Inhibitors of Wild–Type and Mutant Enzymes"; J Med Chem, 1998, vol. 41, pp. 2960–2971.
Kohlstaedt, L. A. et al; "Crystal Structure at 3.5 A Resolution of HIV–1 Reverse Transcriptase Complexed with an Inhibitor"; Science; 1992, vol. 256; pp. 1783–1790.
Berge, S. M. et al; "Pharmaceutical Salts"; J Pharm Sciences; 1977; vol. 66, pp 1–19.
Gero, T. W. et al; "Halogenation of 2–Hydroxynicotinic Acid"; Synthetic Communications; 1989; vol. 19, pp. 553–559.
Warren, T. C. et al; "Comparative Purification of Recombinant HIV–1 and HIV–2 Reverse Transcriptase: Preparation of Heterodimeric Enzyme Devoid of Unprocessed Gene Product"; Protein Expression and Purification; 1992; vol. 3, pp. 479–487.
Simoneau, B.; "Non–Nucleoside Reverse Transcriptase Inhibitors"; US 2002/0028807 A1; published Mar. 7, 2002.
Ogilvie, W. W., et al; "Non–Nucleoside Reverse Transcriptase Inhibitors"; US 2003/0069226 A1; published Apr. 10, 2003.

*Primary Examiner*—Bruck Kifle
(74) *Attorney, Agent, or Firm*—Robert P. Raymond; Alan R. Stempel; Michael P. Morris

(57) ABSTRACT

Disclosed are compounds of formula I:

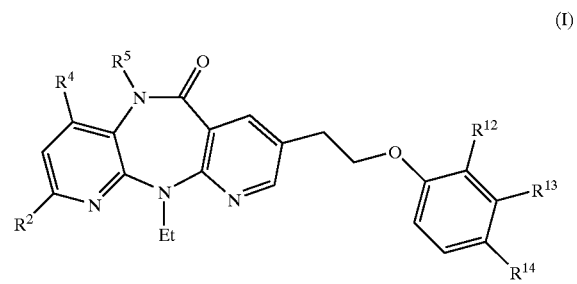

(I)

wherein
  $R^2$ is H, halogen, $(C_{1-4})$alkyl, $O(C_{1-4})$alkyl, $NH(C_{1-4}$alkyl) or $N(C_{1-4}$alkyl)$_2$;
  $R^4$ is H or $CH_3$;
  $R^5$ is H or $CH_3$;
  $R^{12}$ is H, halogen, $(C_{1-4})$alkyl, $CF_3$, or $NO_2$;
  $R^{13}$ is H, $(C_{1-4})$alkyl, halogen, OH, or $NH_2$, with the proviso that $R^{12}$ and $R^{13}$ are not both H; and
  $R^{14}$ is COOR$^{14a}$ wherein $R^{14a}$ is H or $(C_{1-6})$alkyl; or $R^{14}$ is $(C_{2-4})$alkenyl-COOR$^{14a}$
  wherein $R^{14a}$ is as defined herein; or $R^{14}$ is $(C_{1-4})$alkyl-COOR$^{14a}$ wherein $R^{14a}$ is as defined above;
or a salt or a prodrug thereof, useful as inhibitors of HIV reverse transcriptase.

23 Claims, No Drawings

NON-NUCLEOSIDE REVERSE TRANSCRIPTASE INHIBITORS

RELATED APPLICATIONS

Benefit of U.S. Provisional Application, Serial No. 60/367,971, filed on Mar. 27, 2002, is hereby claimed.

TECHNICAL FIELD OF THE INVENTION

The invention concerns novel compounds and pharmaceutically acceptable salts thereof, their use, either alone or in combination with other therapeutic agents, in the treatment or prophylaxis of HIV infection, and to pharmaceutical compositions comprising the compounds.

BACKGROUND OF THE INVENTION

The disease known as acquired immune deficiency syndrome (AIDS) is caused by the human immunodeficiency virus (HIV), particularly the strain known as HIV-1. In order for HIV to be replicated by a host cell, the information of the viral genome must be integrated into the host cell's DNA. However, HIV is a retrovirus, meaning that its genetic information is in the form of RNA. The HIV replication cycle therefore requires a step of transcription of the viral genome (RNA) into DNA, which is the reverse of the normal chain of events. An enzyme that has been aptly dubbed reverse transcriptase (RT) accomplishes the transcription of the viral RNA into DNA. The HIV virion includes a copy of RT along with the viral RNA.

Reverse transcriptase has three known enzymatic functions; it acts as an RNA-dependent DNA polymerase, as a ribonuclease, and as a DNA-dependent DNA polymerase. Acting as an RNA-dependent DNA polymerase, RT transcribes a single-stranded DNA copy of the viral RNA. Acting as a ribonuclease, RT destroys the original viral RNA, and frees the DNA just produced from the original RNA. Finally, acting as a DNA-dependent DNA polymerase, RT makes a second, complementary DNA strand, using the first DNA strand as a template. The two strands form double-stranded DNA, which is integrated into the host cell's genome by another enzyme called integrase.

Compounds that inhibit the enzymatic functions of HIV-1 reverse transcriptase will inhibit replication of HIV-1 in infected cells. Such compounds are useful in the prevention or treatment of HIV-1 infection in human subjects, as demonstrated by known RT inhibitors such as 3'-azido-3'-deoxythymidine (AZT), 2',3'-dideoxyinosine (ddI), 2',3'-dideoxycytidine (ddC), d4T, 3TC, Nevirapine, Delavirdine, Efavirenz and Abacavir, the main drugs thus far approved for use in the treatment of AIDS.

As with any antiviral therapy, use of RT inhibitors in the treatment of AIDS eventually leads to a virus that is less sensitive to the given drug. Resistance (reduced sensitivity) to these drugs is the result of mutations that occur in the reverse transcriptase segment of the pol gene. Several mutant strains of HIV have been characterized, and resistance to known therapeutic agents is due to mutations in the RT gene. Some of the most commonly observed mutants in the clinic are: the Y181C mutant, in which a tyrosine (Y) at codon 181 has been mutated to a cysteine (C) residue and K103N where the lysine (K) at position 103 has been replaced by asparagine (N). Other mutants, which emerge with increasing frequency during treatment with known antivirals, include the single mutants V106A, G190A, Y188C, and P236L; and the double mutants K103N/Y181C, K103N/P225H, K103N/V108I, and K103N/L100I.

Continued use of antiviral compounds to prevent HIV infection will undoubtedly cause an increased emergence of new resistant strains of HIV. There is therefore an ongoing need for new inhibitors of RT, with different patterns of effectiveness against the various mutants.

Compounds having tricyclic structures, which are inhibitors of HIV-1, are described in U.S. Pat. No. 5,366,972. Other inhibitors of HIV-1 reverse transcriptase are described in Hargrave et al., J. Med. Chem., 34, 2231 (1991).

U.S. Pat. No. 5,705,499 proposes 8-arylalkyl- and 8-arylheteroalkyl-5,11-dihydro-6H-dipyrido[3,2-B:2',3'-E][1,4]diazepines as inhibitors of RT. The exemplified compounds are shown to have some activity against wild type and mutant HIV-1 RT, particularly Y181C and other single mutants such as K103N albeit less effectively.

WO 01/96338A1 and U.S. Pat. No. 6,420,359 disclose diazepine structures having quinoline and quinoline-N-oxide substituents as inhibitors of RT. The exemplified compounds have activity against HIV WT, single and double mutant strains.

SUMMARY OF THE INVENTION

The invention provides substituted benzoic acid containing compounds that are potent inhibitors of wild-type (WT) and double mutant strains of HIV-1 RT, particularly the double mutation K103N/Y181C.

In a first aspect of the invention, there is provided a compound of formula I:

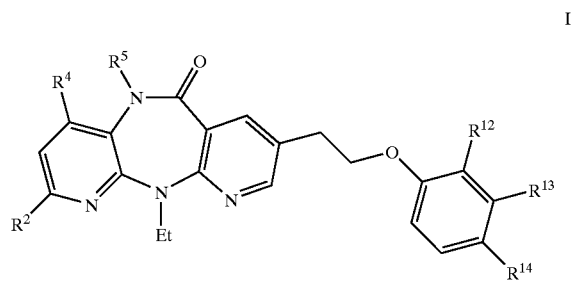

I wherein $R^2$ is H, halogen, $(C_{1-4})$alkyl, $O(C_{1-4})$alkyl, $NH(C_{1-4}$alkyl) or $N(C_{1-4}$alkyl$)_2$;

$R^4$ is H or $CH_3$;

$R^5$ is H or $CH_3$;

$R^{12}$ is H, halogen, $(C_{1-4})$alkyl, $CF_3$, or $NO_2$;

$R^{13}$ is H, $(C_{1-4})$alkyl, halogen, OH, or $NH_2$, with the proviso that $R^{12}$ and $R^{13}$ are not both H; and $R^{14}$ is $COOR^{14a}$ wherein $R^{14a}$ is H or $(C_{1-6})$alkyl; or $R^{14}$ is $(C_{2-4})$alkenylCOOR$^{14a}$ wherein $R^{14a}$ is as defined herein; or $R^{14}$ is $(C_{1-4})$alkylCOOR$^{14a}$ wherein $R^{14a}$ is as defined herein;

or a salt or a prodrug thereof

According to a second aspect of the invention, there is provided a pharmaceutical composition for the treatment or prevention of HIV infection, comprising a compound of formula I, as described herein, or a pharmaceutically acceptable salt thereof, and a pharmaceutically acceptable carrier.

According to a third aspect of the invention, there is provided a method for the treatment or prevention of HIV infection, comprising administering to a patient an HIV inhibiting amount of a compound of formula I or a pharmaceutically acceptable salt thereof, or a pharmaceutical composition, both as defined herein.

According to a fourth aspect of the invention, there is provided a method for treating or preventing HIV infection comprising administering a pharmaceutical composition comprising a compound of formula I, as described herein, in combination with an antiretroviral drug.

According to a fifth aspect of the invention, there is provided a method for preventing perinatal transmission of HIV-1 from mother to baby, comprising administering a compound of formula I or a pharmaceutical composition, as described herein, to the mother before giving birth.

DETAILED DESCRIPTION OF THE INVENTION

Definitions

The following definitions apply unless otherwise noted:

As used herein, the terms "$(C_{1-2})$alkyl", "$(C_{1-4})$alkyl" and "$(C_{1-6})$alkyl", either alone or in combination with another radical, is intended to mean acyclic alkyl radicals containing up to two, four, or six carbon atoms respectively. Examples of such radicals include methyl, ethyl, propyl, butyl, 1-methylethyl, 1-methylpropyl, 2-methylpropyl, and 1,1-dimethylethyl.

As used herein, the term "$(C_{2-4})$alkenyl", either alone or in combination with another radical, is intended to mean an unsaturated, acyclic radical containing two to four carbon atoms.

As used herein, the term "halogen" means a halogen atom and includes fluorine, chlorine, bromine and iodine.

As used herein, the term "pharmaceutically acceptable salt" includes those derived from pharmaceutically acceptable bases and is non-toxic. Examples of suitable bases include choline, ethanolamine and ethylenediamine. $Na^+$, $K^+$, and $Ca^{++}$ salts are also contemplated to be within the scope of the invention (also see Pharmaceutical salts, Birge, S. M. et al., J. Pharm. Sci., (1977), 66, 1–19, incorporated herein by reference).

As used herein, the term "prodrug" refers to pharmacologically acceptable derivatives, such that the resulting biotransformation product of the derivative is the active drug, as defined in compounds of formula I. Examples of such derivatives include, but are not limited to, esters and amides. (see Goodman and Gilman in The Pharmacological Basis of Therapeutics, $9^{th}$ ed., McGraw-Hill, Int. Ed. 1995, "Biotransformation of Drugs, p 11–16, incorporated herein by reference).

Detailed Description of Preferred Embodiments

Preferably, $R^2$ is H, halogen, $(C_{1-4})$alkyl, $O(C_{1-4})$alkyl or $N(C_{1-4}alkyl)_2$. Even preferably, $R^2$ is H, Cl, F, $(C_{1-4})$alkyl, $O(C_{1-4})$alkyl, or $N(C_{1-4}alkyl)_2$. More preferably $R^2$ is H, Cl, F, $CH_3$, OMe, or OEt. Most preferably, $R^2$ is H.

Preferably, $R^4$ and $R^5$ are not both the same.

More preferably, $R^4$ is H.

More preferably, $R^5$ is $CH_3$.

Preferably, $R^{12}$ is halogen, $(C_{1-4})$alkyl, $CF_3$, or $NO_2$. More preferably, $R^{12}$ is Br, Cl, $CH_3$ or $CH_3CH_2$. Most preferably, $R^{12}$ is $CH_3$ or $CH_3CH_2$.

Preferably, $R^{13}$ is H, $CH_3$, halogen, OH, or $NH_2$. More preferably, $R^{13}$ is H, $CH_3$, or OH. Most preferably, $R^{13}$ is H.

Preferably, $R^{14}$ is COOH, COOMe, $(C_{2-4})$alkenylCOOH, or $(C_{1-4})$alkylCOOH. More preferably, $R^{14}$ is COOH, CH=CH—COOH, $CH_2$COOH, or $CH_2CH_2$COOH. Most preferably, $R^{14}$ is COOH.

The compounds of formula I are effective inhibitors of wild type HIV as well as inhibiting the double mutant enzyme K103N/Y181C.

The compounds of formula I possess inhibitory activity against HIV-1 reverse transcriptase. When administered in suitable dosage forms, they are useful in the treatment of AIDS, ARC and related disorders associated with HIV-1 infection.

Another aspect of the invention, therefore, is a method for treating HIV-1 infection which comprises administering to a human being, infected by HIV-1, a therapeutically effective amount of a novel compound of formula I, as described above. Whether it be termed treatment or prophylaxis, the compound may also be used to prevent perinatal transmission of HIV-1 from mother to baby, by administration to the mother prior to giving birth.

The compounds of formula I may be administered in single or divided doses by the oral or parenteral routes. A suitable oral dosage for a compound of formula I would be in the range of about 0.5 mg to 3 g per day. A preferred oral dosage for a compound of formula I would be in the range of about 100 mg to 800 mg per day for a patient weighing 70 kg. In parenteral formulations, a suitable dosage unit may contain from 0.1 to 250 mg of said compound, preferably 1 mg to 200 mg. It should be understood, however, that the dosage administration from patient to patient will vary and the dosage for any particular patient will depend upon the clinician's judgement, who will use as criteria for fixing a proper dosage the size and condition of the patient as well as the patient's response to the drug.

When the compounds of the present invention are to be administered by the oral route, they may be administered as medicaments in the form of pharmaceutical preparations, which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The compounds of formula I can be used in combination with an antiretroviral drug known to one skilled in the art, as a combined preparation useful for simultaneous, separate or sequential administration for treating or preventing HIV infection in an individual. Examples of antiretroviral drugs that may be used in combination therapy with compounds of formula I, include but are not limited to, nucleoside/nucleotide reverse transcriptase inhibitors (such as AZT and Tenofovir), non-nucleoside reverse transcriptase inhibitors (such as Nevirapine), protease inhibitors (such as Ritanovir), viral fusion inhibitors (such as T-20), CCR5 antagonists (such as SCH-351125), CXCR4 antagonists (such as AMD-3100), integrase inhibitors (such as L-870,810), TAT inhibitors, other investigational drugs (such as PRO-542, BMS-806, MC-114 or AI-183), antifungal or antibacterial agents (such as fluconazole), and immunomodulating agents (such as Levamisole). Moreover, a compound of formula I can be used with another compound of formula I.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula I can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compound.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenylethyl alcohol.

Additionally, the compounds provided by the invention can be administered by suppository.

Methodology and Synthesis

The compound of the invention may be made using the skills of a synthetic organic chemist. Exemplary reaction schemes are shown in Schemes 1 to 4 below. Substituents $R^2$, $R^4$, $R^5$, $R^{12}$, $R^{13}$, $R^{13}$, and $R^{14}$ are as defined herein,

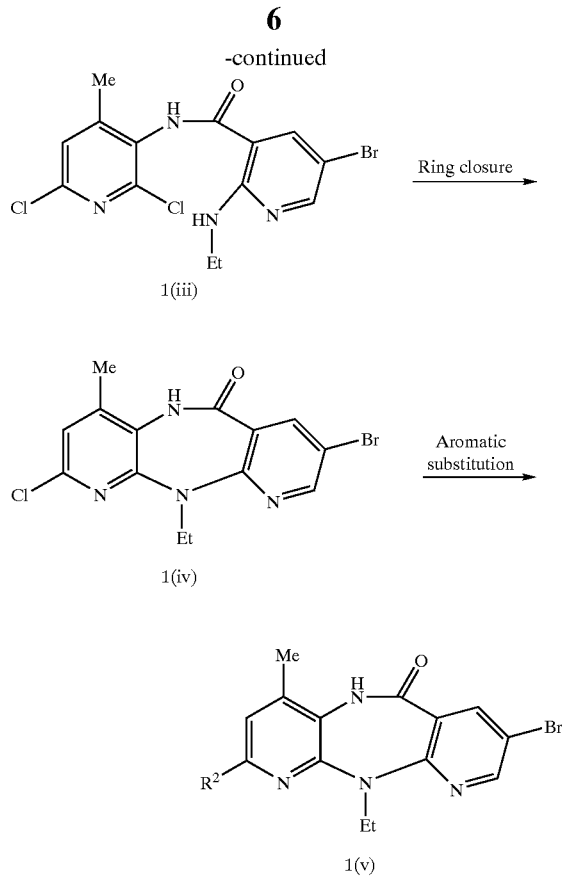

Briefly, aromatic substitution ($S_NAR$) of 1(i) with Et—$NH_2$ produces intermediate 1(ii). Thereafter, halogenation of the 5-position using a brominating agent (for example, NBS or bromine) gives 1(iii). Ring closure of 1(iii) via a base-mediated $S_nAR$ reaction forms the tricyclic intermediate 1(iv). Introduction of the $R^2$ substituent proceeds via an aromatic substitution of the C-2 chlorine in 1(iv) thereby giving compound of intermediate 1(v).

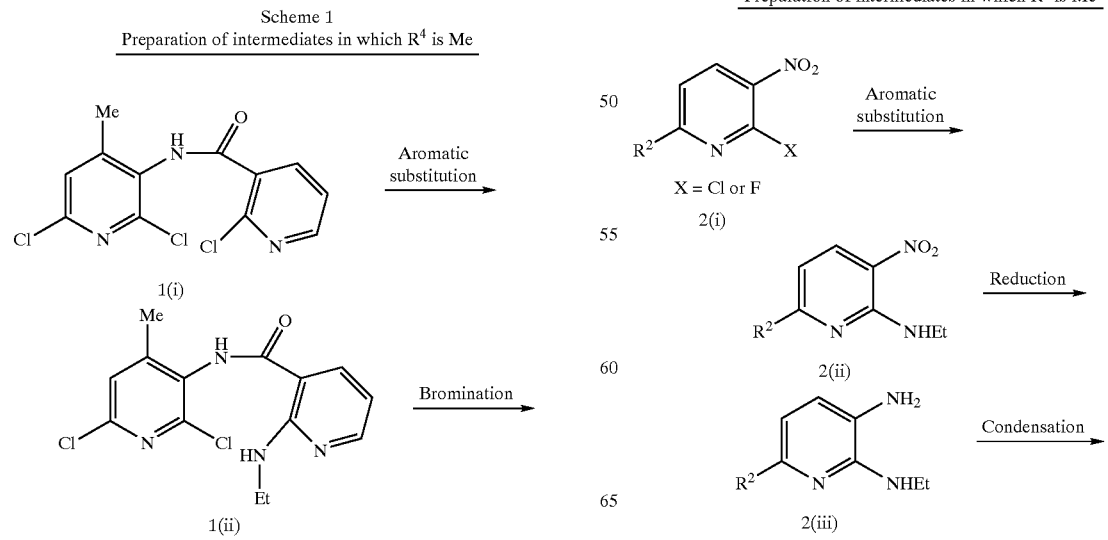

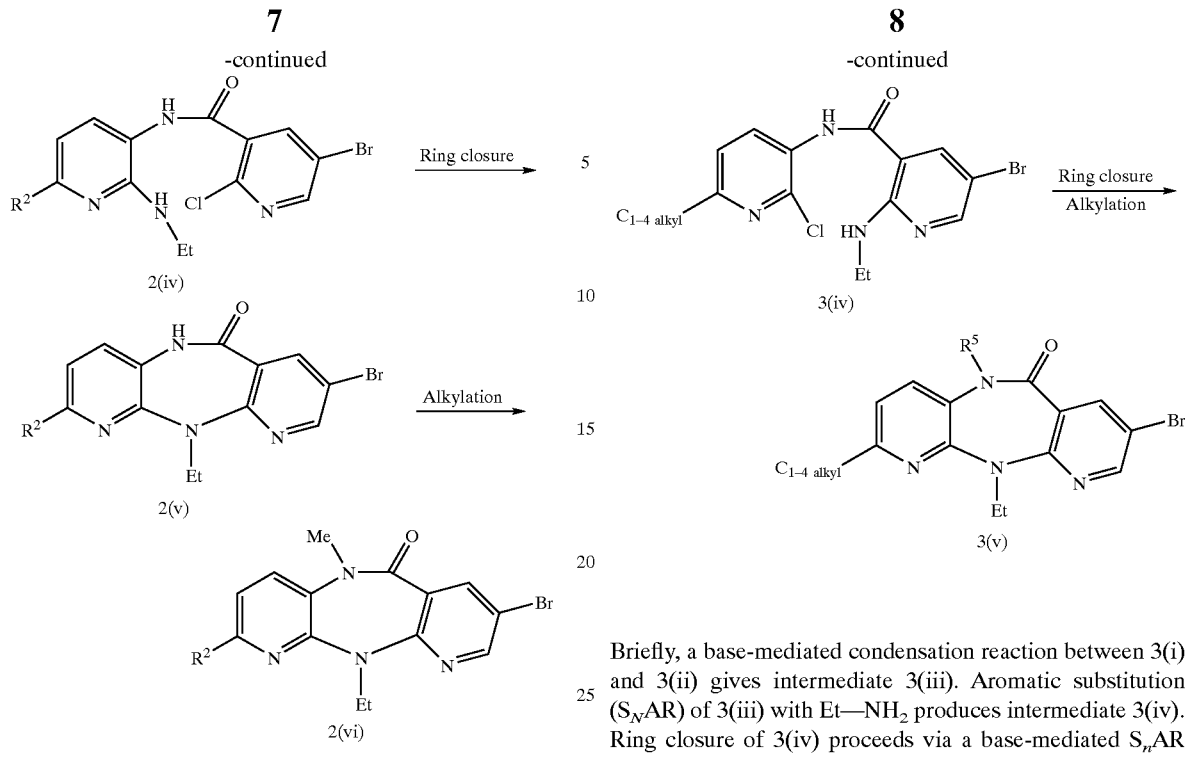

The sequence of scheme 2 is analogous to one described by J. M. Klunder et al.; *J. Med. Chem.* 1998, 41, 2960–71, and C. L. Cywin et al.; *J. Med. Chem.* 1998, 41, 2972–84. Briefly, aromatic substitution ($S_NAR$) of 2(i) with Et—$NH_2$ produces intermediate 2(ii). Reduction of the nitro group (for example using catalytic hydrogenation) produces 2(iii). A base mediated condensation reaction of 2(iii) with, for example, 5-bromo-2-chloro-3-pyridinecarbonyl chloride, provides 2(iv). Ring closure of 2(iv) proceeds via a base-mediated $S_nAR$ reaction to form the tricyclic intermediate 2(v). The $R^5$ methyl group in 2(vi) may be introduced by art recognized alkylation using, for example, methyl iodide.

Briefly, a base-mediated condensation reaction between 3(i) and 3(ii) gives intermediate 3(iii). Aromatic substitution ($S_NAR$) of 3(iii) with Et—$NH_2$ produces intermediate 3(iv). Ring closure of 3(iv) proceeds via a base-mediated $S_nAR$ reaction to form a tricyclic intermediate, which is alkylated to give compound of intermediate 3(v).

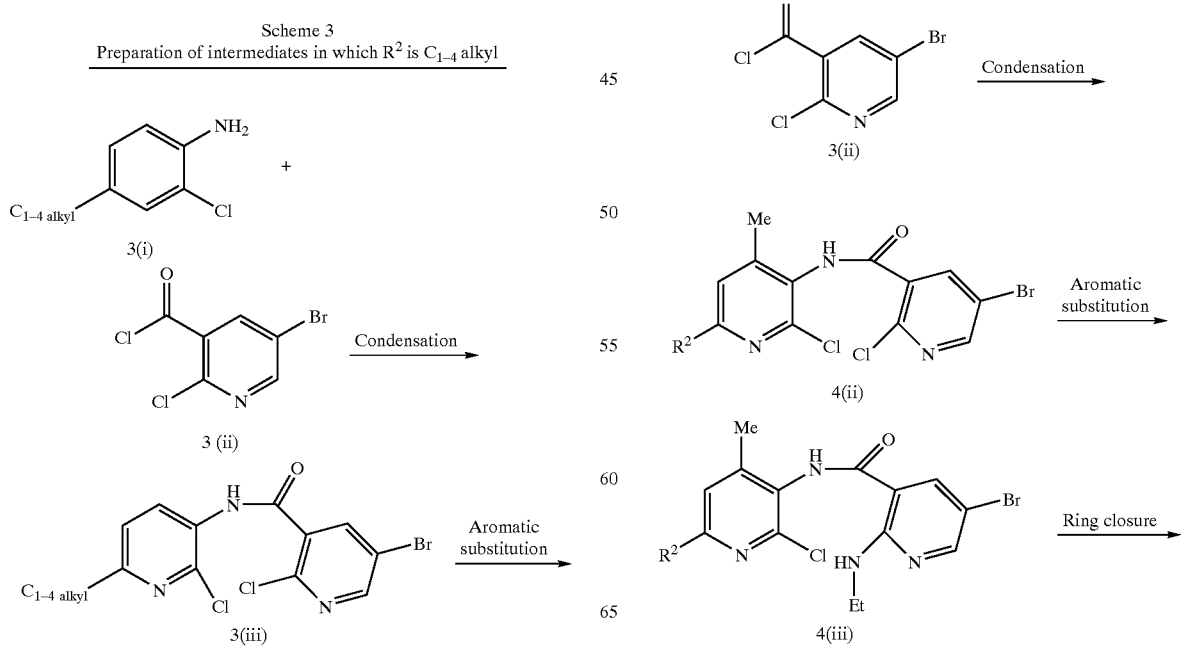

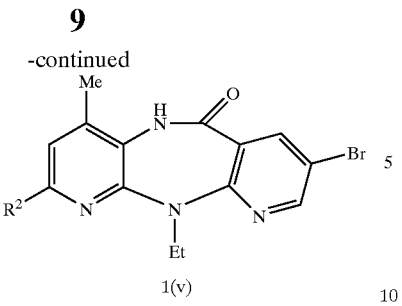

1(v)

Briefly, a base-mediated condensation reaction between 4(i) and 3(ii) gives intermediate 4(ii). Aromatic substitution ($S_NAR$) of 4(ii) with $Et-NH_2$ produces intermediate 4(iii). Ring closure of 4(iii) proceeds via a base-mediated $S_nAR$ reaction to form a tricyclic compound of intermediate 1(v).

inhibit the RNA-dependent DNA polymerase activity of HIV-1 RT. Certain specific compound described in the Examples which appear below, were so tested. The results of this testing appear in Table 1 as $IC_{50}$ and $EC_{50}$.

EXAMPLES

The present invention is illustrated in further detail by the following non-limiting examples. All reactions were performed in a nitrogen or argon atmosphere unless otherwise stated. Temperatures are given in degrees Celsius. Solution percentages or ratios express a volume to volume relationship, unless stated otherwise.

Abbreviations or symbols used herein include:
DEAD: diethyl azodicarboxylate;
DIAD: diisopropyl azodicarboxylate;
DIEA: diisopropylethylamine;

Scheme 5
Introduction of the benzoic acid derivatives

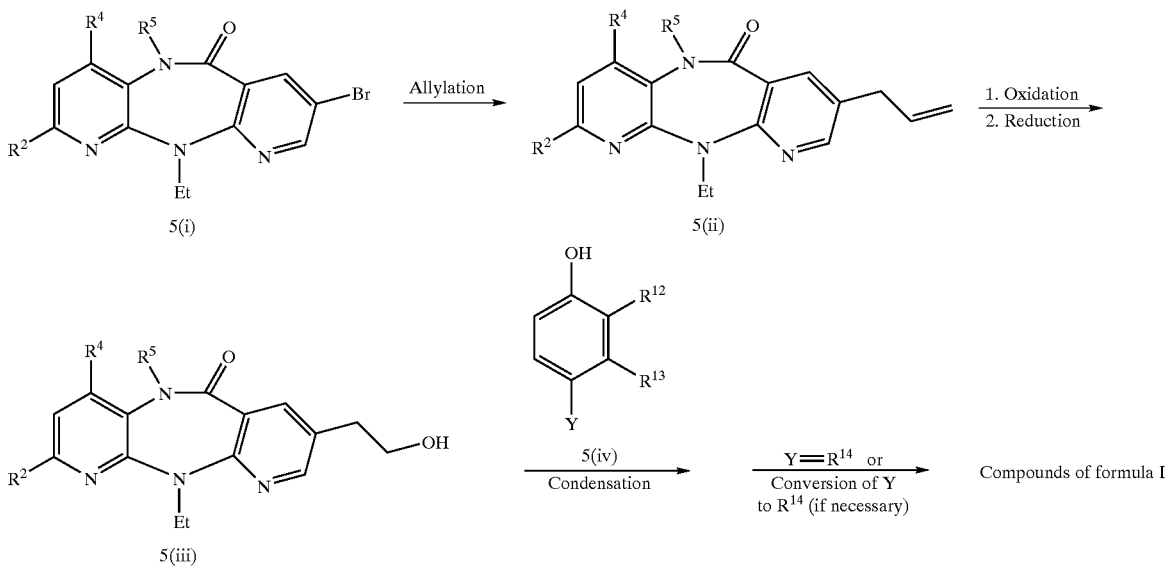

Briefly, cross-coupling of bromo derivative 5(i), synthesized as described herein, with an allyl tin reagent in an aprotic solvent (e.g. DMF) and in the presence of a catalyst, forms C-8 substituents 5(ii). Oxidation of the double bond (e.g. by ozonolysis to produce an ozonide), followed by a reduction, produces the C-8 hydroxyethyl substituent 5(iii). Using a Mitsunobu-type reaction, naphthyl derivatives 5(iv), 5(v) or 5(vi) when Y is $R^{14}$ with the exception of COOH, are condensed with 5(iii) to produce compound of formula I. Alternatively, when Y is a $R^{14}$ group precursor, for example $COOCH_3$, a Mitsunobu-type reaction can be used to condense 5(iv) or 5(v) with 5(iii), and thereafter Y can be chemically converted into $R^{14}$ substituents, for example by saponification of $COOCH_3$ to give COOH, thereby giving compound of formula I.

As stated before, the compound provided by the invention inhibit the enzymatic activity of HIV-1 RT. Based upon testing of these compound, as described below, it is known that they inhibit the RNA-dependent DNA polymerase activity of HIV-1 RT. It is known (data not shown) that they also inhibit the DNA-dependent DNA polymerase activity of HIV-1 RT. Utilizing the Reverse Transcriptase (RT) Assay described below, compound can be tested for their ability to DMAP: 4-(dimethylamino)pyridine;
DMSO: dimethylsulfoxide;
DMF: dimethylformamide;
DCC: dicyclohexylcarbodiimide;
ES MS: electron spray mass spectrometry;
Et: ethyl;
EtOH: ethanol;
EtOAc: ethyl acetate;
$Et_2O$: diethyl ether;
HPLC: high performance liquid chromatography;
iPr: isopropyl;
Me: methyl;
MeOH: methanol;
MeCN: acetonitrile;
NaHMDS: sodium hexamethyldisilazide;
NBS: N-bromosuccinimide;
Ph: phenyl;
TBE: tris-borate-EDTA;
TBTU: 2-(1H-benzotriazol-1-yl)-N,N,N',N'-tetramethyluronium tetrafluoroborate;

TFA: trifluoroacetic acid;
THF: tetrahydrofuran;
PFU: plaque-forming units;
DEPC: diethyl pyrocarbonate;
DTT: dithiothreitol;
EDTA: ethylenediaminetetraacetate;
UMP: uridine 5'-monophosphate;
UTP: uridine 5'-triphosphate;
MES: 2-(n-morpholino)ethanesulfonic acid;
SDS-PAGE: sodium dodecyl sulfate-polyacrylamide gel electrophoresis;
MWCO: molecular weight cut-off;
Bis-Tris Propane: 1,3-Bis{tris(hydroxymethyl)-methylamino}propane;
GSH: reduced glutathione;
OBG: n-Octyl-β-D-glucoside.

Syntheses

The following examples illustrate methods for preparing compounds of the invention.

Example 1

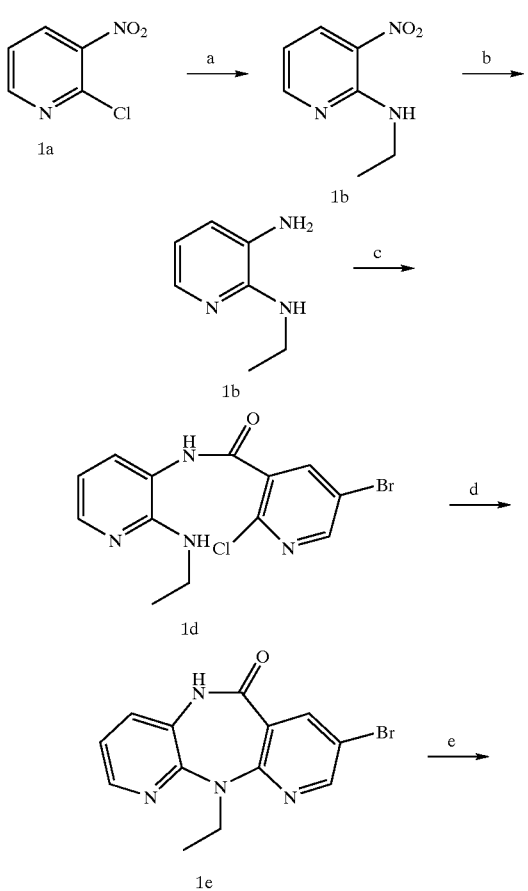

Step a:
To a solution of 2-chloro-3-nitropyridine 1a (51 g, 325 mmol) in THF (650 mL) was added a 2 M solution of ethylamine in THF (365 mL, 731 mmol). The reaction was stirred at room temperature overnight. The reaction mixture was poured into water (~1.5 L) and the resulting solid was filtered and dried under reduced pressure to give compound 1b (52 g).

Step b:
A solution of 2-(ethylamino)-3-nitropyridine 1b (52 g) in MeOH (600 mL) was stirred overnight at room temperature under hydrogen (1 atm.) in the presence of 20% Pd(OH)$_2$/C (10.4 g). The catalyst was removed by filtration through diatomaceous earth. The filtrate was concentrated under reduced pressure to give compound 1c as a black solid (39 g, 88% yield over steps a and b).

Step c:
To a cooled solution of 3-amino-2-(ethylamino)pyridine 1c (30.6 g, 223 mmol) in MeCN (740 mL) was added solid NaHCO$_3$ (56.3 g, 669 mmol). After 5 min, crude 5-bromo-2-chloro-3-pyridinecarbonyl chloride (prepared from 5-bromo-2-hydroxy-3-pyridinecarboxylic acid and SOCl$_2$ (1 equiv., 223 mmol) was added [as described by T. W. Gero et al. in *Synth. Commun.* 1989, 19, 553–559 (incorporated herein by reference) but with omission of the aqueous work-up]. After 2 h, the reaction mixture was poured over ice/H$_2$O (1.5 L) and the resulting solid was filtered, rinsed with H$_2$O and then hexane. After drying under reduced pressure overnight, compound 1d was obtained as a black solid (54.9 g, 69% yield).

Step d:
To a solution of 2-chloro-N-{2-(ethylamino)-3-pyridinyl}-5-bromo-3-pyridinecarboxamide 1d (54.9 g, 154.4 mmol) in pyridine (308 mL) at 50° C. was added drop-wise a 1 M solution of NaHMDS in THF (355 mL, 355 mmol). After 10 min, the reaction was allowed to cool to room temperature, and then was poured over ice water (2 L).

The resulting solid was filtered, rinsed with water and then hexane. The solid was dried under reduced pressure to give compound 1e (36 g, 75% yield) as a dark green solid.

Step e:

To a solution of the 8-bromo-5,11-dihydro-11-ethyl-6H-dipyrido[3,2-b:2',3'-e][1,4]diazepin-6-one 1e (36.7 g, 115 mmol) in DMF (380 mL) was added NaH (3.5 g, 138 mmol), and the mixture was heated to 50° C. for 30 min. The reaction mixture was cooled to room temperature and treated with MeI (14.3 mL, 230 mmol). After 1.5 h, the reaction mixture was poured over ice water. The solid was filtered, washed with water and then hexane to give after drying, compound 1f (37.9 g 99% yield) as a dark gray solid.

Step f:

Allyltributyltin (30.7 mL, 99.0 mmol) and Pd(Ph$_3$P)$_4$ (5.20 g, 4.50 mmol) were added to a degassed (N$_2$ through solution for 30 min) solution of 8-bromo-5,11-dihydro-11-ethyl-5-methyl-6H-dipyrido[3,2-b:2',3'-e][1,4]diazepin-6-one 1f (30.0 g, 90.0 mmol) in DMF (450 mL) at room temperature. The mixture was stirred at 90° C. for 1.5 h then was cooled to room temperature and concentrated under reduced pressure. The residue was purified by flash chromatography (hexane: EtOAc, 8:2 to 7:3) to give compound 1g (22.19 g, 84% yield).

Step g:

A stream of ozonized oxygen was bubbled through a cold (–78° C.) solution of 5,11-dihydro-11-ethyl-5-methyl-8-(2-propenyl)-6H-dipyrido[3,2-b:2',3'-e][1,4]diazepin-6-one 1g (22.19 g, 75.4 mmol) in CH$_2$Cl$_2$ (150 mL) and MeOH (150 mL) for 2.5 h. A stream of N$_2$ was next bubbled through the solution for 15 min and then solid NaBH$_4$ (4.99 g, 132 mmol) was added to the solution. The reaction mixture was allowed to warm to room temperature. After 1 h, aqueous saturated NH$_4$Cl (200 mL) was added and the mixture was stirred at room temperature for 2 h. The organic solvents were removed under reduced pressure. Water (300 mL) and CHCl$_3$ (300 mL) were added to the residue. The phases were separated and the aqueous layer was extracted with CHCl$_3$ (3×300 mL). The combined organic layers were dried (MgSO$_4$), filtered and concentrated under reduced pressure. The residue was purified by flash chromatography (EtOAc:CHCl$_3$, 4:1) to give compound 1h (16.1 g, 72% yield) as a white solid.

Example 2

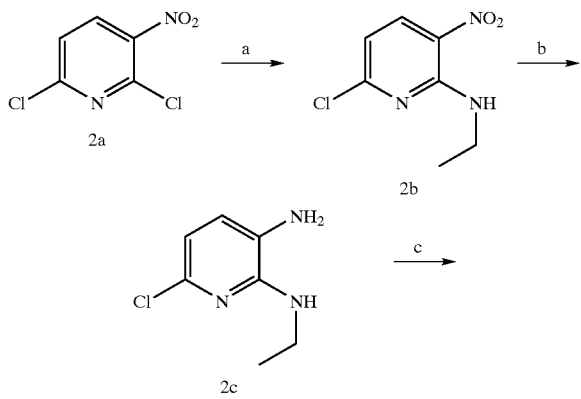

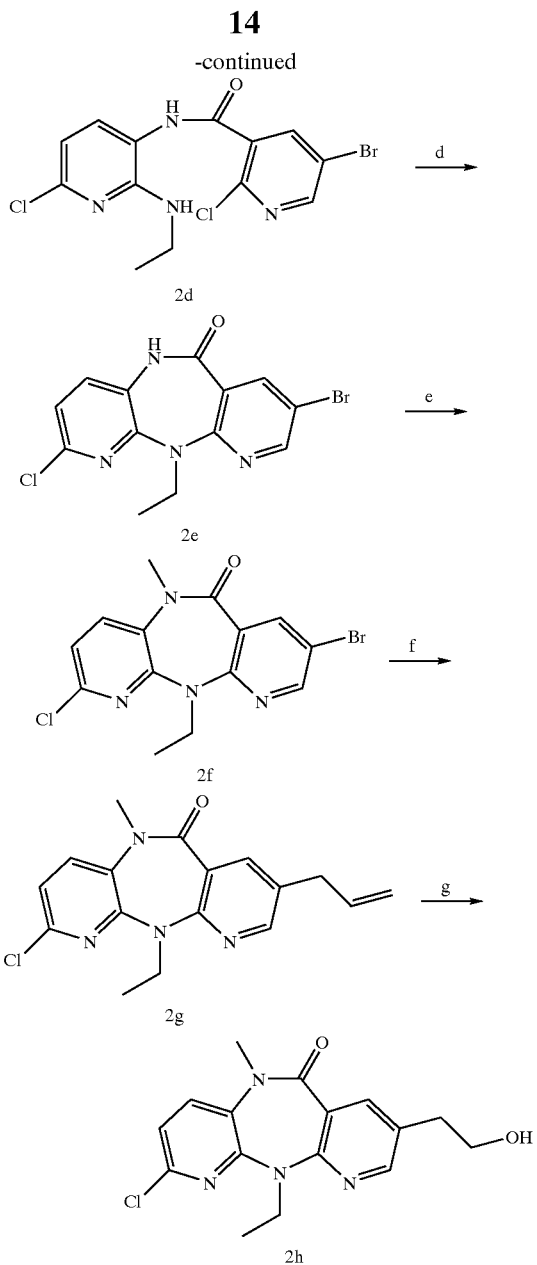

Step a:

An ice-cold solution of EtNH$_2$ (49.8 g, 1.10 mol) in toluene (200 mL) was added over 15 min to an ice-cold solution of 2,6-dichloro-3-nitropyridine 2a (100.0 g, 0.52 mol) in toluene (225 mL). The mixture was stirred at 0° C. for 45 min. Water (500 mL) and EtOAc (500 mL) were added and the phases were separated. The organic layer was successively washed with water (200 mL) and brine (200 mL), dried (MgSO$_4$), filtered and concentrated under reduced pressure. The residual solid was recrystallized from MeOH to give compound 2b (83.7 g, 80% yield) as yellow needles.

Step b:

Compound 2c was prepared in a manner analogous to Example 1, step b.

Step c:

A solution of 5-bromo-2-chloro-3-pyridinecarbonyl chloride (30.0 g, 97.0 mmol) in MeCN (100 mL) was added via cannula to a solution of 3-amino-6-chloro-2-(ethylamino) pyridine 2c (16.6 g, 97.0 mmol) in MeCN (180 mL) containing solid NaHCO₃ (14.2 g, 169 mmol) at room temperature. The mixture was stirred at room temperature for 1 h. Water (200 mL) was added and the mixture was stirred for 10 min. The resulting suspension was filtered. The solid was washed with water then hexane and dried under reduced pressure to give compound 2d (28.4 g, 75% yield).

Step d:

A 1 M solution of NaHMDS in THF (167.5 mL, 167.5 mmol) was slowly added to a solution of 5-bromo-2-chloro-N-{2-(ethylamino)-6-chloro-3-pyridinyl}-3-pyridinecarboxamide 2d (28.4 g, 72.8 mmol) in pyridine (146 mL) heated to 50° C. The reaction mixture was stirred at 50° C. for 1.5 h. The mixture was then poured into a mixture of water and ice (1 L) and, after 1 h, the resulting suspension was filtered. The solid washed with water and dried under reduced pressure to give compound 2e (23.4 g, 91% yield).

Step e:

Solid NaH (60% oil dispersion, 3.46 g, 86.1 mmol) was added over 30 min to a solution of 8-bromo-2-chloro-5,11-dihydro-11-ethyl-6H-dipyrido[3,2-b:2',3'-e][1,4]diazepin-6-one 2e (23.4 g, 66.3 mmol) in DMF (220 mL) at 50° C. The mixture was stirred at 50° C. for 1 h then was allow to cool to room temperature. The mixture was poured into water (1 L) and the resulting suspension was filtered. The solid was successively washed with water and hexane then dried under reduced pressure to give compound 2f (23.0 g, 94% yield).

Step f:

Allyltributyltin (21.3 mL, 68.7 mmol) and Pd(Ph₃P)₄ (3.61 g, 3.12 mmol) were added to a degassed (N₂ through solution for 30 min) solution of 8-bromo-2-chloro-5,11-dihydro-11-ethyl-5-methyl-6H-dipyrido[3,2-b:2',3'-e][1,4]diazepin-6-one 2f (23.0 g, 62.5 mmol) in DMF (312 mL). The mixture was heated to 90° C. for 2 h. The mixture was concentrated under reduced pressure. The residue was purified by flash chromatography (hexane:EtOAc, 7:3) to give compound 2g (13.4 g, 65% yield).

Step g:

ozonized oxygen was introduced into a cold (−78° C.) solution of 2-chloro-5,11-dihydro-11-ethyl-5-methyl-8-(2-propenyl)-6H-dipyrido[3,2-b:2',3'-e][1,4]diazepin-6-one 2g (13.4 g, 40.7 mmol) in MeOH (102 mL) and CH₂Cl₂ (102 mL) until complete disappearance of the alkene. Nitrogen was bubbled through the solution to remove excess O₃. Solid NaBH₄ (2.69 g, 71.1 mmol) was next added in small portions and the mixture was allowed to warm slowly to room temperature. After 1 h, aqueous saturated NH₄Cl (150 mL) was added and the mixture stirred for 20 min. The organic solvents were removed under reduced pressure. Water (100 mL) was added to the aqueous solution. The solution was extracted with CHCl₃ (3×200 mL). The combined organic layers were dried (MgSO₄), filtered and concentrated under reduced pressure. The residue was purified by flash chromatography (EtOAc:CHCl₃, 4:1) to give compound 2h (10.4 g, 77% yield).

Example 3

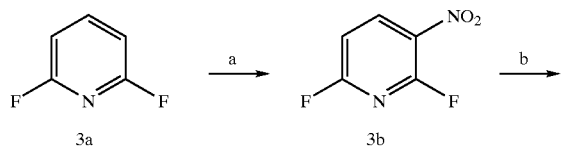

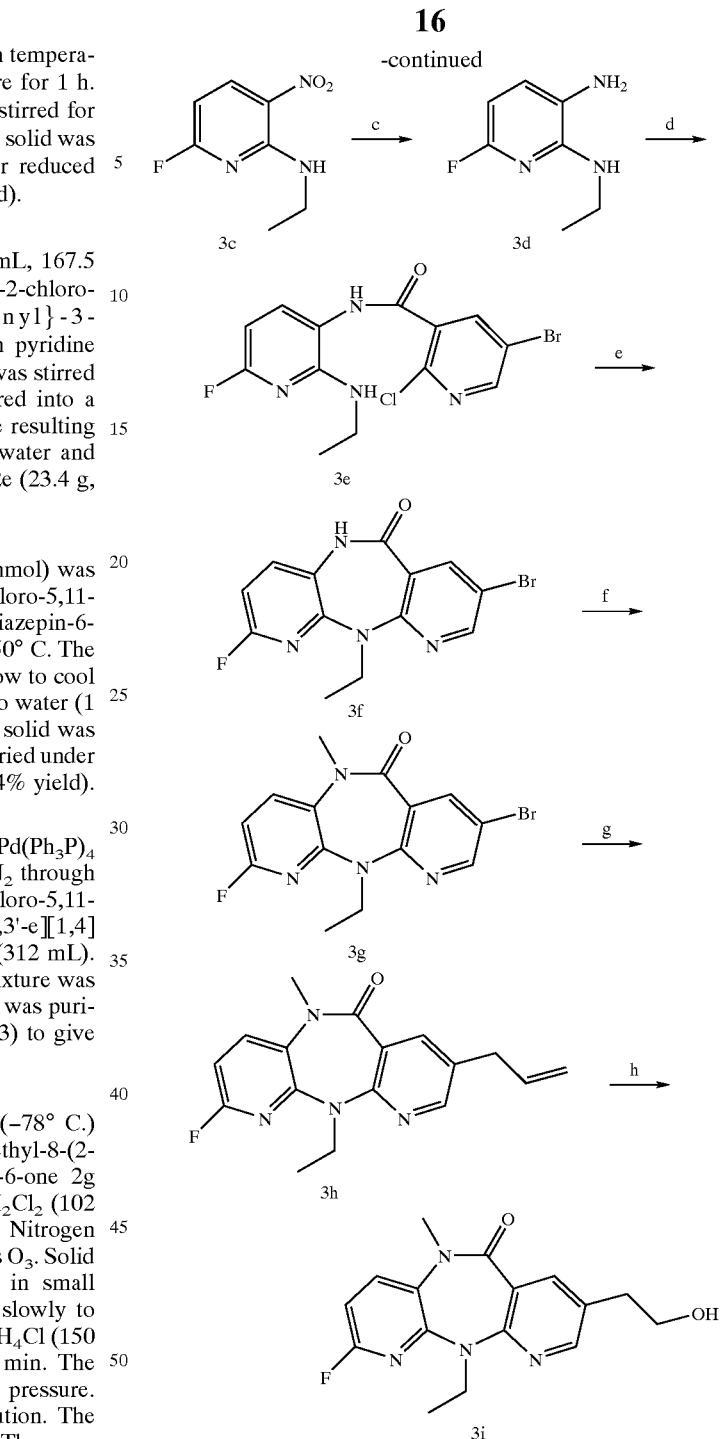

Step a:

To a mixture of concentrated sulphuric acid (600 mL) and fuming nitric acid (90%, 400 mL) in a ice-bath (internal temperature maintained at 5–10° C.) was added drop-wise 2,6-difluoropyridine 3a (200 g, 1.74 mol). The resulting mixture was stirred overnight at room temperature. The mixture was poured slowly into 3 kg of ice and extracted with Et₂O (2×2 L). The combined organic layers were washed with aqueous 1.5 N NaOH (2×1 L), then with aqueous saturated NaHCO₃ (400 mL) or until pH is around 8–9. The organic layers were dried over MgSO₄, filtered and concentrated under reduced pressure until constant weight (to remove unreacted 2,6-difluoropyridine: 10–12%). Compound 3b was obtained as a yellow liquid (207.3 g, 74% yield).

Step b:

To a solution of 2,6-difluoro-3-nitropyridine 3b (45.7 g, 285 mmol) in THF (500 mL) at −40° C. was added dropwise a solution of ethylamine (25.7 g, 570 mmol) in THF (250 mL). After 30 min, the reaction mixture was concentrated under reduced pressure and the residue was dissolved in EtOAc. The organic phase was washed with brine, dried ($MgSO_4$), filtered and concentrated. The resulting yellow solid was purified by flash chromatography (15% EtOAc in hexane) to give compound 3c (43.2 g, 82% yield) as a yellow solid.

Step c:

A solution of 2-ethylamino-6-fluoro-3-nitropyridine 3c (43.2 g, 230 mmol) in THF (1 L) was stirred overnight at room temperature under hydrogen (1 atm.) in the presence of 20% $Pd(OH)_2/C$ (4.35 g). The catalyst was removed by filtration through diatomaceous earth. The filtrate was concentrated under reduced pressure to give compound 3d (36.3 g, 95% yield) as a black solid.

Step d:

To a cooled solution (4° C.) of 3-amino-2-ethylamino-6-fluoropyridine 3d (31.0 g, 200 mmol) in MeCN (160 mL) was added solid $NaHCO_3$ (50.4 g, 600 mmol). After 15 min, a solution of 5-bromo-2-chloro-3-pyridinecarbonyl chloride (1 equiv., 200 mmol) in MeCN (155 mL) was added. After 60 min at room temperature, the reaction mixture was poured into water (1.2 L) and stirred for 30 min. The resulting solid was filtered, dried under reduced pressure at 50° C. overnight. Compound 3e (73.7 g, 99% yield) was obtained as a black solid.

Step e:

To a solution of the 2-chloro-N-{2-(ethylamino)-6-fluoro-3-pyridinyl}-5-bromo-3-pyridinecarboxamide 3e (73.5 g, 216 mmol) in pyridine (435 mL) at 50° C. was added drop-wise a 1 M solution of NaHMDS in THF (520 mL. 520 mmol). After 10 min, the reaction was allowed to cool to room temperature, then poured over ice water (2 L). The resulting solid was filtered, rinse with water and then hexane. The solid was dried under reduced pressure to give compound 3f (50.6 g, 69% yield) as a dark green solid.

Step f:

To a solution of the 8-bromo-5,11-dihydro-11-ethyl-2-fluoro-6H-dipyrido[3,2-b:2',3'-e][1,4]diazepin-6-one 3f (44 g, 130.5 mmol) in DMF (520 mL) was added NaH (4.28 g, 178 mmol), and the mixture was heated to 50° C. for 30 min. The reaction mixture was cooled to room temperature and treated with MeI (24.4 mL, 522 mmol). After 1.5 h, the reaction mixture was poured over ice water. The solid was filtered, washed with water and then hexane, dried under reduced pressure to give compound 3g (43.2 g, 94% yield) as dark gray solid.

Step g:

Allyltributyltin (32.0 mL, 103.4 mmol) and $Pd(Ph_3P)_4$ (5.43 g, 4.70 mmol) were added to a degassed ($N_2$ through solution for 45 min) solution of 8-bromo-5,11-dihydro-11-ethyl-2-fluoro-5-methyl-6H-dipyrido[3,2-b:2',3'-e][1,4]diazepin-6-one 3g (33.0 g, 94.0 mmol) in DMF (470 mL). Additional amounts of $Pd(Ph_3)_4$ (1.09 g, 0.94 mmol) were added after 1, 2, 3, 4 and 5 h to complete the reaction. The mixture was heated to 90° C. for 6 h. The mixture was concentrated under reduced pressure. The residue was purified by flash chromatography (hexane:EtOAc, 8:2 to 7:3) to give compound 3h (22.4 g, 76% yield).

Step h:

A stream of ozonized oxygen was bubbled through a cold (−78° C.) solution of 5,11-dihydro-11-ethyl-2-fluoro-5-methyl-8-(2-propenyl)-6H-dipyrido[3,2-b:2',3'-e][1,4]diazepin-6-one 3h (22.38 g, 71.6 mmol) in $CH_2Cl_2$ (100 mL) and MeOH (100 mL) for 3 h. A stream of $N_2$ was next bubbled through the solution for 15 min and then solid $NaBH_4$ (5.05 g, 133 mmol) was added to the solution. The reaction mixture was allowed to warm to room temperature. After 1 h, an additional portion of $NaBH_4$ (1.62 g, 43.0 mmol) was added to the reaction mixture. After an additional hour, aqueous saturated $NH_4Cl$ (150 mL) was added and the mixture was stirred at room temperature for 30 min. The organic solvents were removed under reduced pressure. Water (200 mL) was added and the mixture was extracted with $CHCl_3$ (3×300 mL). The combined organic layers were dried ($MgSO_4$), filtered and concentrated under reduced pressure. The residue was purified by flash chromatography (EtOAc:$CHCl_3$, 4:1) to give compound 3l (19.7 g, 72% yield) as a white solid.

Example 4 (Entries 1003 and 1031)

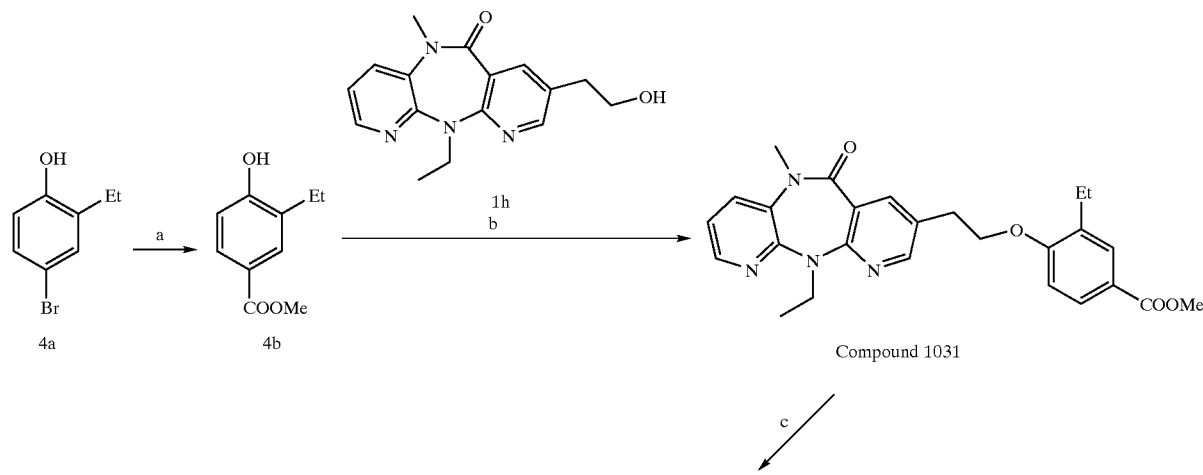

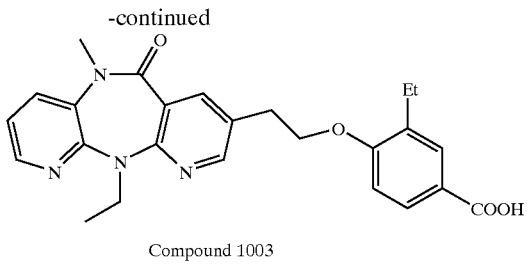

Compound 1003

Step a:

A solution of 1.6 M n-BuLi in hexane (6.22 mL, 9.95 mmol) was added rapidly to a cold (−78° C.) solution of 4a (0.87 g, 4.33 mmol) in THF (20 mL). The mixture was stirred at −78° C. for 10 min, allowed to warm to 0° C. and maintained at 0° C. for 1 h. A stream of $CO_2$ was introduced into the reaction mixture for 10 min and the solution was rendered acidic by addition of aqueous 1.0 N HCl solution. The mixture was extracted with EtOAc. The organic layer was dried ($MgSO_4$), filtered and concentrated under reduced pressure. The residue was taken in $Et_2O$ (20 mL) and treated with excess $CH_2N_2$ solution in $Et_2O$ (ca. 0.6 M, 10 mL) for 10 min. The mixture was concentrated under reduced pressure and the residue was purified by flash chromatography (hexane:EtOAc, 4:1 to 7:3) to give 4b (0.13 g, 17% yield).

Step b:

A solution of DIAD (86 μL, 0.44 mmol) in THF (2.0 mL) was added over 30 min to a solution of 1h (100 mg, 0.33 mmol), 4b (60.0 mg, 0.33 mmol) and $PPh_3$ (114 mg, 0.44 mmol) in THF (10 mL) at 25° C. The mixture was stirred for 1 h then was concentrated under reduced pressure. The residue was purified by flash chromatography (hexane:EtOAc, 7:3 to 1:1) to give compound 1031 (128 mg, 83% yield).

Step c:

A aqueous 1.0 N LiOH solution (1.52 mL, 1.52 mmol) was added to a solution of compound 1031 (100 mg, 0.22 mmol) in THF (6 mL) and MeOH (2 mL). The reaction mixture was stirred at 25° C. for 24 h then was heated to reflux for 1 h. The solution was rendered acidic by addition of aqueous 1.0 N HCl solution then extracted with EtOAc. The organic layer was washed with water (2×) and brine, dried ($MgSO_4$), filtered and concentrated under reduced pressure. The residue was triturated with $Et_2O$/hexane to give compound 1003 (80 mg, 83% yield) as a white solid. A mixture of compound 1003 (38.0 mg, 0.085 mmol) and aqueous 0.02 N NaOH solution (4.3 mL, 0.085 mmol) in MeCN (3 mL) was sonicated. The resulting solution was frozen and lyophilized to give the corresponding sodium salt (37 mg, 98% yield) as a white solid.

Example 5 (Entries 1019, 1020 and 1028)

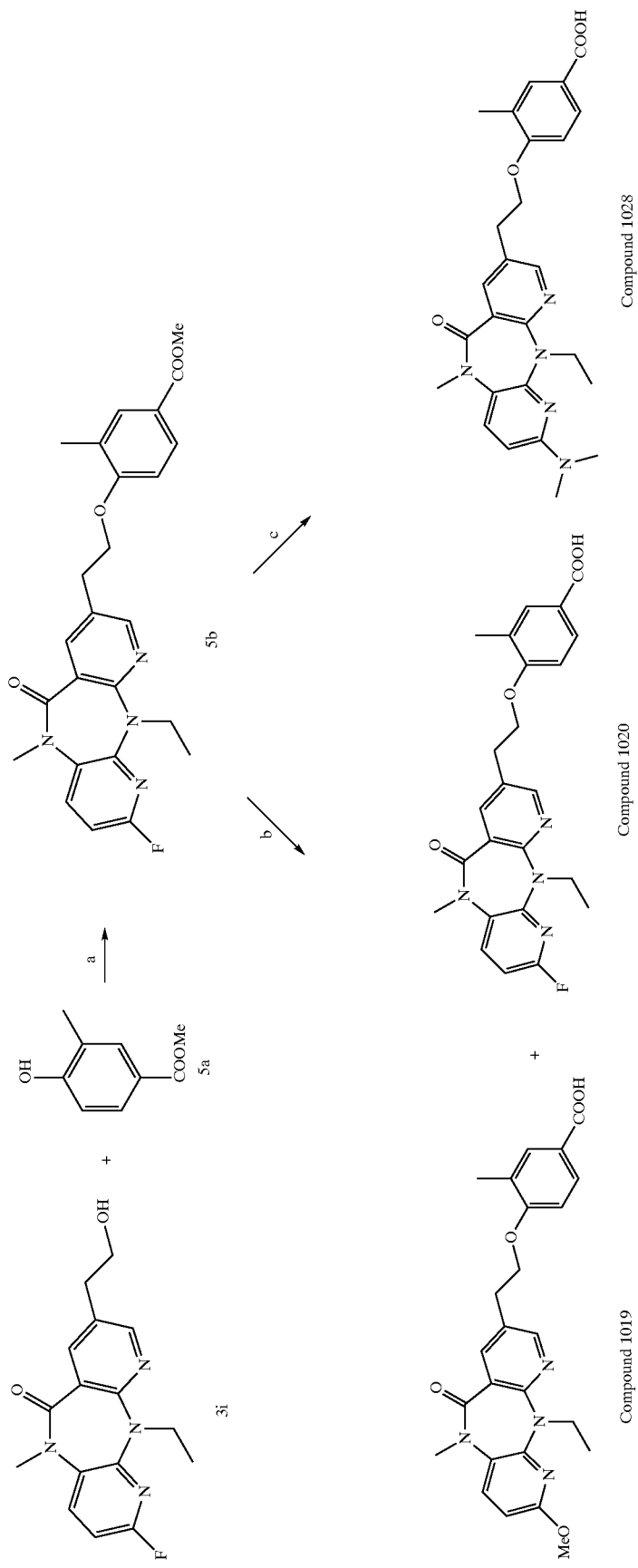

Step a:

A solution of DIAD (86 µL, 0.44 mmol) in THF (2.0 mL) was added over 2 h to a solution of 3i (106 mg, 0.34 mmol), 5a (56.0 mg, 0.34 mmol) and PPh$_3$ (114 mg, 0.44 mmol) in THF (7 mL) at 25° C. The mixture was stirred for 1 h then was concentrated under reduced pressure. The residue was purified by flash chromatography (hexane:EtOAc, 7:3 to 1:1) to give 5b (115 mg, 73% yield) as a white solid.

Step b:

A aqueous 1.0 N LiOH solution (1.0 mL, 1.0 mmol) was added to a solution of 5b (100 mg, 0.21 mmol) in MeOH (6 mL). The reaction mixture was stirred at 25° C. for 24 h. The solution was rendered acidic by addition of aqueous 1.0 N HCl solution then extracted with EtOAc. The organic layer was washed with water and brine, dried (MgSO$_4$), filtered and concentrated under reduced pressure. The residue was purified by flash chromatography (hexane:EtOAc:AcOH, 50:50:1) to give first compound 1019 (25 mg, 25% yield) as a white solid followed by compound 1020 (48 mg, 50% yield) as a white solid. The corresponding sodium salts were obtained by treatment with aqueous 0.02 N NaOH.

Step c:

A 1.0 M dimethylamine solution in THF (5.0 mL, 5.0 mmol) and a aqueous 1.0 N LiOH solution (1.0 mL, 1.0 mmol) were added to a solution of 5b (50.0 mg, 0.11 mmol) in i-PrOH (3 mL). The reaction mixture was heated to reflux for 48 h. Aqueous 1.0 N HCl solution (2 mL) was added and the mixture was extracted with EtOAc. The organic layer was washed with water and brine, dried (MgSO$_4$), filtered and concentrated under reduced pressure. The residue was purified by flash chromatography (hexane:EtOAc:AcOH, 50:50:1) to give compound 1028 (18 mg, 35% yield) as a white solid. The corresponding sodium salt was obtained by treatment with aqueous 0.02 N NaOH.

Example 6 (Entry 1014)

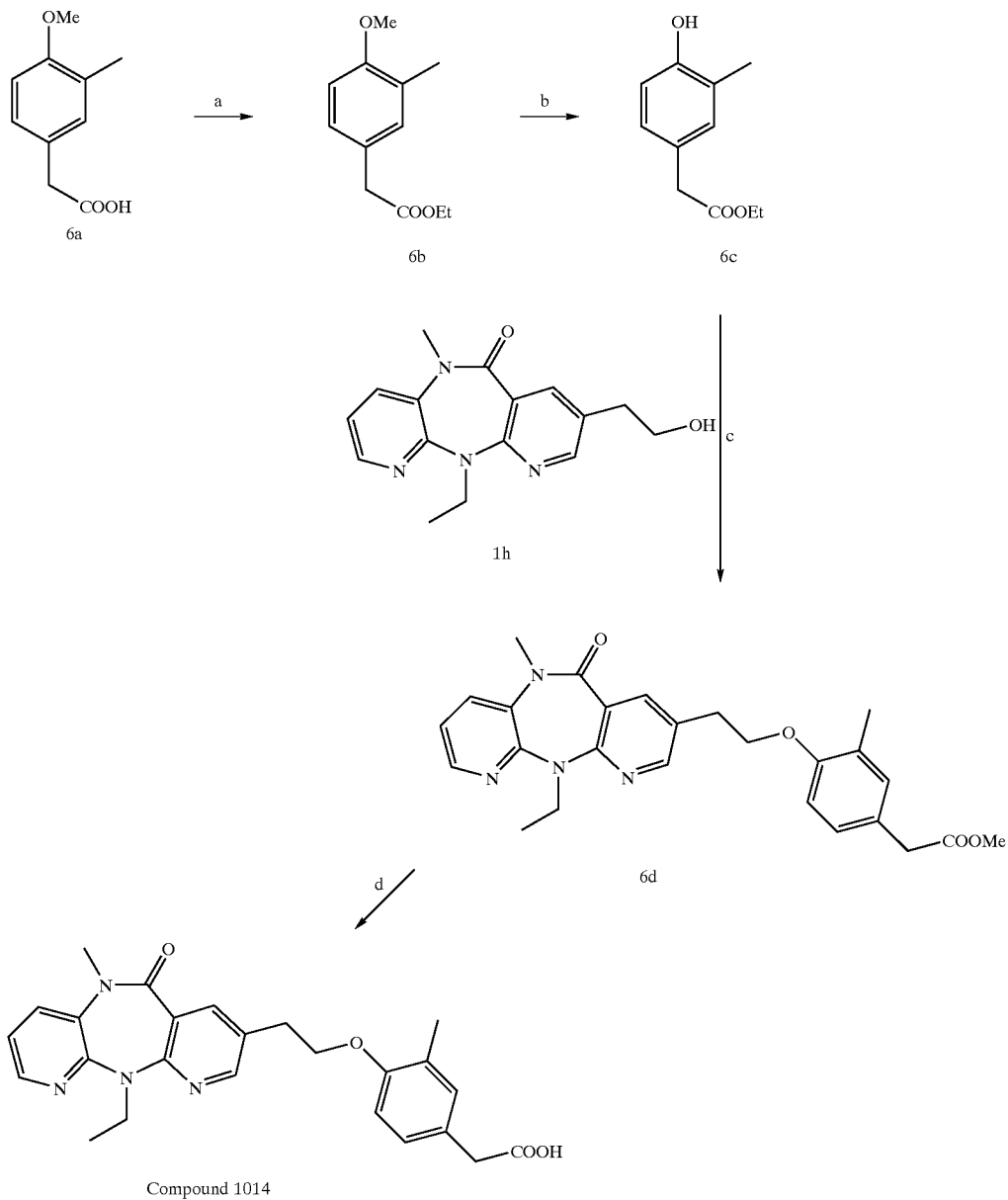

Compound 1014

Step a:

To a solution of acid 6a (1.00 g, 5.55 mmol) in $CH_2Cl_2$ (50 mL) was added oxalyl chloride (0.73 mL, 8.3 mmol) and DMF (100 µL). The reaction was stirred for 90 min then EtOH (15 mL) was added, and the reaction was stirred an additional hour. The reaction mixture was concentrated under reduced pressure, the residue was diluted with EtOAc and successively washed with water, brine, dried (MgSO4), filtered, and concentrated to give ester 6b used without further purification.

Step b:

To a solution of ester 6b in $CH_2Cl_2$ (50 mL) was added a 1 M solution of $BBr_3$ in $CH_2Cl_2$ (7.2 mL, 7.20 mmol). After 3 h at room temperature, the reaction mixture was cooled to 0° C. and EtOH (5 mL) was added. The reaction mixture was stirred for 30 min at room temperature then was concentrated under reduced pressure. The residue was diluted with EtOAc and successively washed with saturated aqueous $NaHCO_3$ solution, water and brine, dried ($MgSO_4$), filtered and concentrated to dryness. The residue was purified by flash chromatography (hexane:EtOAc; 70:30) to give phenol 6c (802 mg, 74% yield over 2 steps) as a clear gum.

Step c:

A solution of DIAD (87 µL, 0.44 mmol) in THF (2.0 mL) was added over 2 h to a solution 1h (100 mg, 0.33 mmol), $Ph_3P$ (104 mg, 0.44 mmol) and phenol 6c (65 mg, 0.34 mol) in THF (7.0 mL) at room temperature. The mixture was stirred for 4 h then concentrated under reduced pressure. The residue was purified by flash chromatography (hexane:EtOAc; 30:70 to 50:50) to give compound 6d (46 mg, 29% yield white foam.

Step d:

To a solution of ester 6d (44 mg, 0.09 mmol) in a mixture of THF (3 mL) and MeOH (1 mL) was added aqueous 1 N LiOH solution (1.0 mL, 1.0 mmol). After 4 h at room temperature, 1 N HCl (2 mL) was added. The mixture was extracted with EtOAc. The organic layer was washed with water and brine, dried ($MgSO_4$), filtered and concentrated to dryness to give compound 1014 (39 mg, 93% yield) as a white solid. The corresponding sodium salt was obtained by treatment with 1 equivalent of aqueous sodium hydroxide, and the resulting solution was lyophilized to give a fluffy white solid.

TABLE 1

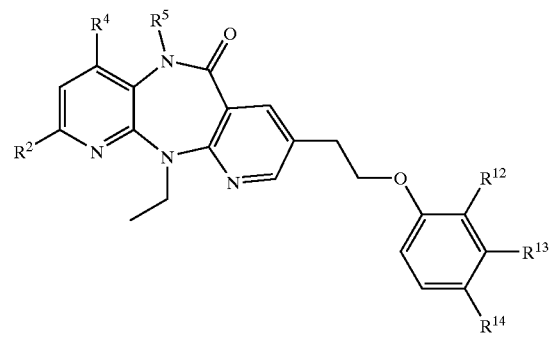

| Cpd. Entry # | $R^2$ | $R^4$ | $R^5$ | $R^{12}$ | $R^{13}$ | $R^{14}$ | MS (ESI) m/z $(MH)^+$ |
|---|---|---|---|---|---|---|---|
| 1001 | H | H | Me | Me | Me | COOH | 447 |
| 1002 | H | H | Me | Me | H | COOH | 433 |
| 1003 | H | H | Me | Et | H | COOH | 447 |
| 1004 | H | H | Me | Me | OH | COOH | 449 |

TABLE 1-continued

| Cpd. Entry # | $R^2$ | $R^4$ | $R^5$ | $R^{12}$ | $R^{13}$ | $R^{14}$ | MS (ESI) m/z $(MH)^+$ |
|---|---|---|---|---|---|---|---|
| 1005 | H | H | Me | Br | H | COOH | 497/499 |
| 1006 | H | H | Me | Me | H | CHMeCOOH | 461 |
| 1007 | Cl | H | Me | Me | H | $CH_2CH_2COOH$ | 495/497 |
| 1008 | H | H | Me | Me | H | $CH_2CH_2COOH$ | 461 |
| 1009 | Cl | H | Me | Me | H | CH=CHCOOH | 493/495 |
| 1010 | H | H | Me | Me | H | CH=CHCOOH | 459 |
| 1011 | H | H | Me | Cl | H | $CH_2COOH$ | 467/469 |
| 1012 | H | H | Me | Br | H | $CH_2COOH$ | 511/513 |
| 1013 | H | H | Me | Me | Me | $CH_2COOH$ | 461 |
| 1014 | H | H | Me | Me | H | $CH_2COOH$ | 447 |
| 1015 | Cl | H | Me | Me | H | COOH | 467/469 |
| 1016 | Cl | Me | H | Me | H | COOH | 467/469 |
| 1017 | Me | H | Me | Me | H | COOH | 447 |
| 1018 | H | Me | H | Me | H | COOH | 433 |
| 1019 | OMe | H | Me | Me | H | COOH | 463 |
| 1020 | F | H | Me | Me | H | COOH | 451 |
| 1021 | OEt | H | Me | Me | H | COOH | 477 |
| 1022 | H | H | Me | $NO_2$ | H | COOH | 464 |
| 1023 | H | H | Me | Cl | H | COOH | 453/455 |
| 1024 | H | H | Me | H | $NH_2$ | COOH | 434 |
| 1025 | H | H | Me | H | F | COOH | 437 |
| 1026 | H | H | Me | H | Cl | COOH | 453/455 |
| 1027 | H | H | Me | $CF_3$ | H | COOH | 487 |
| 1028 | $N(Me)_2$ | H | Me | Me | H | COOH | 476 |
| 1029 | H | H | H | Me | H | COOH | 419 |
| 1030 | H | H | Me | Me | H | COOMe | 447 |
| 1031 | H | H | Me | Et | H | COOMe | 461 |
| 1032 | H | H | Me | Cl | H | COOMe | 467/469 |
| 1033 | H | H | Me | $CF_3$ | H | COOMe | 501 |
| 1034 | OEt | H | Me | Me | H | COOMe | 491 |
| 1035 | H | H | Me | H | F | COOMe | 451 |

Reverse Transcriptase (RT) Assays

Assay Theory

Among the enzymes for which Human Immunodeficiency Virus (HIV-1) encodes is a reverse transcriptase (1), so-named because it transcribes a DNA copy from an RNA template. This activity can be quantitatively measured in a cell-free enzyme assay and is based upon the observation that reverse transcriptase is able to use a synthetic template poly r(C) primed with a biotinylated oligo d(G) to transcribe a radio-labeled DNA strand utilizing 3H-dGTP as a substrate. The assay described below utilizes the wild-type enzyme (which is the predominant form of the enzyme observed in patients infected with HIV-1) and can also be used with mutant RT enzymes (for example, Y181C, prepared by site-directed mutagenesis in which the tyrosine residue at codon 181 has been replaced by a cysteine residue) in analogous assay conditions. This assay allows compound to be evaluated for their effectiveness at inhibiting the mutant enzymes.

Materials a) Preparation of the Enzyme

Some HIV-1 IIIB clone BH10 RT mutants were provided by Dr. C.-K. Shih (Boehringer Ingelheim Pharmaceuticals Inc., U.S.A.) in the vector pKK233-2 (Pharmacia). Briefly an HIV RT clone pKRT2 containing only the RT p66 gene regulated by the lac operon/trc promoter was obtained from Dr. W. Summers (Yale University) (2). A variety of specific amino acid substitutions were introduced into the wild-type RT gene by site-directed mutagenesis. RT clones were subcloned into the pKK233-2 bacterial expression vector. Clones provided included wild-type, Val106Ala, Tyr181Cys, Tyr188Cys, Tyr188Leu, Gly190Ala and Pro236Leu. Others were made in-house by site-directed mutagenesis of the pKK233-2 RT clones including Lys103Asn/Tyr181 Cys, Lys103Asn/Leu100Ile, Lys103Asn/Pro225His, and Lys103Asn/Val108Ile.

b) Purification of Enzyme

Purification of recombinant reverse transcriptase was performed using a combination of methods previously described (3). A single colony from a fresh plate of transformed JM109 cells was used to initiate growth of a pre-culture grown o/n at 37° C. Two liters of growth medium were inoculated with this pre-culture. At $OD_{600}$~1.5 (5–6 h at 37° C.), RT gene expression was induced with IPTG (1 mM final), and the fermentation was continued for a few more hours at 37° C. After centrifugation, supernatants were discarded while cell pellets were pooled and stored at −0° C. until purification. Cells were thawed at 4° C. overnight and suspended in lysis buffer (MES 50 mM pH 6, EDTA 1 mM, 10% v/v glycerol, 0.02% w/v OBG, 0.02% w/v sodium azide). Lysozyme was added and the mixture was incubated on ice for 40 minutes. After homogenization using a Dounce in presence of lysozyme and sonication, the cells were centrifuged for 30 minutes. Supernatant (S1) was saved and stored at 4° C. The centrifuged pellet was resuspended in extraction buffer (MES 50 mM pH 6, $KPO_4$ 50 mM pH 6, KCl 100 mM, 10% v/v glycerol, 0.02% w/v OBG, 0.02% w/v sodium azide) and stirred for 30 minutes at 4° C. This second mixture was centrifuged again and the supernatant (S2) was saved. The above procedure was repeated 2 more times saving supernatants S3 and S4 and one last extraction was performed overnight (S5). Polymin P (0.005% final) was added to the combined supernatants to remove nucleic acids. This solution was stirred for 75 minutes at 4° C. and centrifuged for 1 h. The supernatant (SS1) was precipitated on ice with 20% w/v ammonium sulfate and stirred for 1 h at 4° C. The mixture was then centrifuged and the resulting supernatant (SS2) was precipitated with additional 40% w/v ammonium sulfate (60% total), stirred for 1 h and centrifuged again. The final pellet (P1) was stored overnight at 4° C. before undergoing purification the following day. All steps of the purification were performed at 4° C. unless otherwise stated.

Pellet (P1) was resuspended into MES 50 mM pH 6, $KPO_4$ 10 mM pH 6, KCl 100 mM, 10% v/v glycerol, 0.02% w/v OBG, 0.02% w/v sodium azide. The suspension was dialyzed against the same buffer overnight using 12–14 kD MWCO dialysis tubing. The dialysate was centrifuged and the supernatant was filtered through Millex-PF 0.8 $\mu$m filter units. The filtered sample was loaded on a Hydroxy Apatite column (30-mL bed volume) and washed with the same buffer. The bound enzyme was eluted with ~220 mL of a linear gradient of 10 to 300 mM $KPO_4$ in the above buffer. The fractions containing p66/p51 heterodimer (as determined by SDS-PAGE 8% and Western blotting) were pooled for the next column. The RT containing fractions were diluted two-fold with Bis-Tris propane 50 mM pH 7.0, 0.02% w/v OBG, 10% v/v glycerol, 0.02% w/v sodium azide and loaded on a Hi-Trap Heparin Sepharose column (5-mL bed volume) and washed with the same buffer. The bound RT was then eluted with 75 mL of a linear gradient of 0 to 1 M ammonium sulfate in the same buffer. RT-containing fractions were pooled according to SDS-PAGE and Western blotting analyses. Protein concentration of this pool was determined by the Bradford method using BSA as standard. The final enzyme preparation was dialyzed in MES 50 mM pH 6, $KPO_4$ 300 mM pH 6, KCl 175 mM, 10% v/v glycerol, 0.02% w/v sodium azide and aliquoted and frozen at −80° C.

Assay Procedure

The radiometric enzyme assay has been adapted to a 96-well microtiter plate format and uses streptavidin scintillation proximity beads. The assay is briefly described below. The HIV-1 RT enzyme was thawed and appropriately diluted into Tris/HCl 50 mM pH 7.8 containing NaCl 60 mM, $MgCl_2$ hexahydrate 2 mM, DTT 6 mM, GSH 2 mM and 0.02% w/v Chaps to give ≈3 nM enzyme. To 30 $\mu$L of this enzyme solution was added 10 $\mu$L of inhibitor solution (50 $\mu$M to 2.5 nM inhibitor in same assay buffer as above containing 15% v/v DMSO). The plate was pre-incubated for 15 minutes at room temperature before proceeding to the next step. In this pre-incubation step, the highest and lowest inhibitor concentrations were 12.5 $\mu$M and 0.62 nM respectively and the concentration of DMSO was 3.75% v/v. Then the enzymatic reaction was initiated by addition of 10 $\mu$L of substrate solution. The final reaction mixture contained Tris/HCl 50 mM pH 7.8, NaCl 60 mM, $MgCl_2 \cdot 6H_2O$ 2 mM, DTT 6 mM, GSH 2 mM, Chaps 0.02% w/v DMSO 3% v/v, Poly rC 179 nM, Biotin $dG_{15}$ 18 nM, dGTP 288 nM, $^3$H-dGTP 71 nM, and 1–2 nM enzyme.

In this incubation step, the highest and lowest inhibitor concentrations were 10 $\mu$M and 0.5 nM respectively. After addition of substrates, the plate was covered with a plastic seal and incubated for 1 hour at 37° C. in a dry incubator. Then the reaction was quenched by addition of 75 $\mu$L of EDTA 0.5M containing 5 mg/mL of streptavidin scintillation proximity beads.

The plate was shaken for 2 minutes at medium speed and incubated 1 hour at room temperature. Then 75 $\mu$L of cesium chloride 7 M solution was added, the plate was shaken for 2 minutes at medium speed and incubated again for 1 hour at room temperature. The plate was then covered with a plastic seal and counted using the TopCount-NXT™ Microplate Scintillation & Luminescence Counter, (Packard). Each well was counted for 60 seconds. Each row contained at its extremities a blank and a control well.

The calculation for percent inhibition is as follows:

$$\%\cdot inhibition = \left(1 - \left[\frac{cpm \cdot well - cpm \cdot blank}{cpm \cdot control - cpm \cdot blank}\right]\right) * 100$$

Using the above assay, compound of the invention was tested for inhibition of RT wild-type (WT) and mutant enzymes. The results are listed in Table 4, as $IC_{50}$ (nM).

To confirm the ability of the compound to inhibit HIV replication, it was also tested in the human T-Cell Culture (Syncytia) Assay described below.

ELISA Assay for Assessment of Activity in Cell Culture

The compound of the invention was tested for its ability to inhibit HIV replication in cell culture in a 96-well plate assay. Complete RPMI 1640, consisting of RPMI 1640+ 10% fetal bovine serum, 10 µg/ml gentamycin and 10 µM β-mercaptoethanol was used for dilution of the compound as well as cell growth medium. The T lymphocyte cell line C8166 was infected at a multiplicity of infection of 0.001 with viruses coding for wild type and mutant reverse transcriptase. Cells were then incubated for three days in the presence of serial dilutions of the compound of the invention. The supernatant was pooled from eight replica wells and the concentration of extracellular p24 was determined using a commercially available HIV-1 p24 antigen assay kit (Beckman-Coulter®). The level of inhibition (% inhibition) was calculated with the following equation:

$$\% \cdot inhibition = \left(1 - \left[\frac{p24pg/mL \cdot inhibitor}{p24pg/mL \cdot control}\right]\right) * 100$$

The results are listed in Table 2, as $EC_{50}$ (nM).

References (Incorporated Herein by Reference)

1. Benn, S., et al. Science 230:949, 1985.
2. D'Aquila, R. T. and Summers, W. C. J. Acq. Imm. Def. Syn. 2:579, 1989.
3. a) Warren, T. C. et al. Protein Expression & Purification 3:479, 1992; b) Kohlstaedt, L. A. Science 256(5065): 1783, 1992.

TABLE 2

Inhibition of Wild type and mutant strains of RT for compound of formula I

| Entry # | $IC_{50}$ (WT) (nM) | $IC_{50}$ K103N/ Y181C (nM) | $EC_{50}$ (WT) (nM) | $EC_{50}$ K103N/ Y181C (nM) |
| --- | --- | --- | --- | --- |
| 1001 | C | A | C | C |
| 1002 | C | A | C | C |
| 1003 | C | A | C | C |
| 1004 | C | A | C | A |
| 1005 | C | A | C | C |
| 1006 | C | A | NT | NT |
| 1007 | C | B | C | B |
| 1008 | C | A | C | A |
| 1009 | C | C | C | C |
| 1010 | C | C | C | C |
| 1011 | C | A | NT | NT |
| 1012 | C | A | NT | NT |
| 1013 | C | A | NT | NT |
| 1014 | C | A | C | A |
| 1015 | C | B | C | C |
| 1016 | C | A | NT | NT |
| 1017 | C | A | C | C |
| 1018 | C | A | C | C |
| 1019 | C | A | C | C |
| 1020 | C | A | C | C |
| 1021 | C | A | NT | NT |
| 1022 | B | A | B | A |
| 1023 | B | A | C | A |
| 1024 | C | A | NT | NT |
| 1025 | B | NT | NT | NT |
| 1026 | B | NT | NT | NT |
| 1027 | B | A | NT | NT |
| 1028 | C | A | NT | NT |
| 1029 | C | A | C | NT |
| 1030 | C | C | C | C |
| 1031 | C | C | NT | NT |
| 1032 | C | C | NT | NT |
| 1033 | C | A | NT | NT |

TABLE 2-continued

Inhibition of Wild type and mutant strains of RT for compound of formula I

| Entry # | $IC_{50}$ (WT) (nM) | $IC_{50}$ K103N/ Y181C (nM) | $EC_{50}$ (WT) (nM) | $EC_{50}$ K103N/ Y181C (nM) |
| --- | --- | --- | --- | --- |
| 1034 | C | B | NT | NT |
| 1035 | C | A | NT | NT |

Table legend:
$IC_{50}$ and $EC_{50}$: A = >100 nM; B 100 nM–50 nM; C = <50 nM; and NT = Not tested

What is claimed is:
1. A compound of formula I:

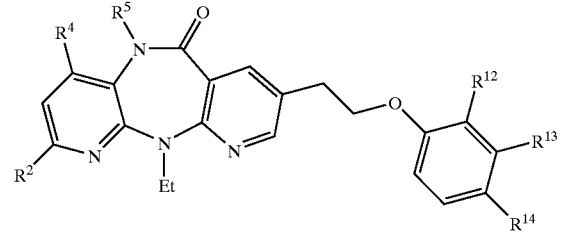

(I)

wherein
$R^2$ is H, halogen, $(C_{1-4})$alkyl, $O(C_{1-4})$alkyl, $NH(C_{1-4}$alkyl) or $N(C_{1-4}$alkyl$)_2$;
$R^4$ is H or $CH_3$;
$R^5$ is H or $CH_3$, provided that $R^4$ and $R^5$ are not both the same;
$R^{12}$ is H, halogen, $(C_{1-4})$alkyl, $CF_3$, or $NO_2$;
$R^{13}$ is H, $(C_{1-4})$alkyl, halogen, OH, or $NH_2$, with the proviso that $R^{12}$ and $R^{13}$ are not both H; and
$R^{14}$ is COOR$^{14a}$ wherein $R^{14a}$ is H or $(C_{1-6})$alkyl; or $R^{14}$ is $(C_{2-4})$alkenyl-COOR$^{14a}$ wherein $R^{14}$ is as defined herein; or $R^{14}$ is $(C_{1-4})$alkyl-COOR$^{14a}$ wherein $R^{14a}$ is as defined above;
or a salt thereof.

2. The compound according to claim 1, wherein $R^2$ is H, halogen, $(C_{1-4})$alkyl, $O(C_{1-4})$alkyl or $N(C_{-4}$alkyl$)_2$ and $R^4$ and $R^5$ are not both the same.

3. The compound according to claim 2, wherein $R^2$ is H, Cl, F, $(C_{1-4})$alkyl, $O(C_{1-4})$alkyl, or $(N(C_{1-4})$alkyl$)_2$.

4. The compound according to claim 3, wherein $R^2$ is H, Cl, F, $CH_3$, OMe, or OEt.

5. The compound according to claim 4, wherein $R^2$ is H.

6. The compound according to claim 1, wherein $R^4$ is H.

7. The compound according to claim 1, wherein $R^5$ is $CH_3$.

8. The compound according to claim 1, wherein $R^{12}$ is halogen, $(C_{1-4})$alkyl, $CF_3$, or $NO_2$.

9. The compound according to claim 8, wherein $R^{12}$ is Br, Cl, $CH_3$ or $CH_3CH_2$.

10. The compound according to claim 9, wherein $R^{12}$ is $CH_3$ or $CH_3CH_2$.

11. The compound according to claim 1, wherein $R^{13}$ is H, $CH_3$, halogen, OH, or $NH_2$.

12. The compound according to claim 11, wherein $R^{13}$ is H, $CH_3$, or OH.

13. The compound according to claim 12, wherein $R^{13}$ is H.

14. The compound according to claim 1, wherein $R^{14}$ is COOH, COOMe, $(C_{2-4})$alkenyl-COOH, or $(C_{1-4})$alkyl-COOH.

15. The compound according to claim 14, wherein $R^{14}$ is COOH, CH=CH—COOH, $CH_2COOH$, or $CH_2CH_2COOH$.

16. The compound according to claim 15, wherein $R^{14}$ is COOH.

17. A compound of formula (I) according to claim 1:

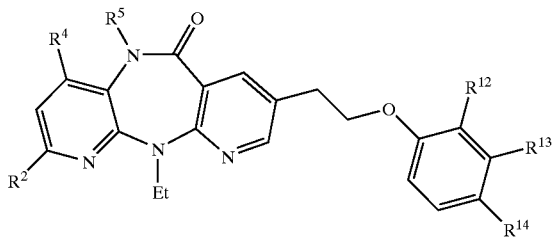

(I)

wherein
$R^2$ is H, Cl, F, $CH_3$, OMe or OEt; $R^4$ is H; $R^5$ is $CH_3$; $R^{12}$ is Br, Cl, $CH_3$ or $CH_2CH_3$; $R^{13}$ H, $CH_3$ or OH; and $R^{14}$ is COOH, CH=CH—COOH, $CH_2COOH$ or $CH_2CH_2COOH$; or a salt thereof.

18. A compound according to claim 17, wherein $R^2$ is H; $R^4$ is H; $R^5$ is $CH_3$; $R^{12}$ is $CH_3$ or $CH_3CH_2$; $R^{13}$ is H; and $R^{14}$ is COOH; or a salt thereof.

19. A pharmaceutical composition comprising a compound of formula I, according to claim 1, or a pharmaceutically acceptable salt thereof, and a pharmaceutically acceptable carrier.

20. A method for the treatment of HIV infection, comprising administering to a patient an HIV inhibiting amount of a compound of formula I, according to claim 1, or a pharmaceutically acceptable salt thereof.

21. A method for the treatment of HIV infection, comprising administering to a patient an HIV inhibiting amount of a pharmaceutical composition, according to claim 19, or a pharmaceutically acceptable salt thereof.

22. A method for treating HIV infection comprising administering a compound of formula I, according to claim 1, in combination with an antiretroviral drug.

23. A method for preventing perinatal transmission of HIV-1 from mother to baby, comprising administering a compound of formula I, according to claim 1, to the mother before giving birth.

* * * * *